(12) United States Patent
Foucault et al.

(10) Patent No.: US 8,182,690 B2
(45) Date of Patent: May 22, 2012

(54) CENTRIFUGAL PARTITIONING CHROMATOGRAPHY DEVICE AND METHOD IMPLEMENTED BY THIS DEVICE

(75) Inventors: Alain Paul Olivier Foucault, Saint-Nazaire (FR); Jack Legrand, Saint-Nazaire (FR); Luc Marchal, Saint-Nazaire (FR); Charles Elie Pierre Agaise, Nantes (FR)

(73) Assignee: Centre National de la Recherche Scientifique, Paris (FR)

( * ) Notice: Subject to any disclaimer, the term of this patent is extended or adjusted under 35 U.S.C. 154(b) by 16 days.

(21) Appl. No.: 12/742,509

(22) PCT Filed: Nov. 6, 2008

(86) PCT No.: PCT/FR2008/001561
§ 371 (c)(1),
(2), (4) Date: Jun. 16, 2010

(87) PCT Pub. No.: WO2009/092914
PCT Pub. Date: Jul. 30, 2009

(65) Prior Publication Data
US 2010/0252503 A1    Oct. 7, 2010

(30) Foreign Application Priority Data
Nov. 13, 2007    (FR) ..................... 07 07975

(51) Int. Cl.
*B01D 15/08*    (2006.01)
(52) U.S. Cl. ..................... 210/635; 210/657; 210/198.2
(58) Field of Classification Search .................. 210/635, 210/656, 657, 659, 198.2
See application file for complete search history.

(56) References Cited

U.S. PATENT DOCUMENTS 4,551,251 A * 11/1985 Kolobow et al. .............. 210/635
(Continued)

FOREIGN PATENT DOCUMENTS

FR    2 791 578 A1    10/2000
(Continued)

OTHER PUBLICATIONS

Ikehata, J. et al., *Effect of Coriolis Force on Counter-Current Chromatographic Separation by Centrifugal Partition Chromatography*, Journal of Chromatography A, 1025, (2004), pp. 169-175.

*Primary Examiner* — Ernest G Therkorn
(74) *Attorney, Agent, or Firm* — Alston & Bird LLP

(57) ABSTRACT

The present invention relates to a centrifugal partitioning chromatography device for separating a liquid having at least two phases, and to a centrifugal partitioning chromatography method implemented by this device. A chromatography device according to the invention comprises at least one flat ring (103) which can be rotated about its axis (X'X) of symmetry and comprises a multitude of cells (110) through which the liquid is intended to flow, each cell being provided with two input/output channels (111 and 112) that are intended to make the liquid flow from one cell to another and which open respectively via two inlet/outlet orifices (111a and 112a) of the cell on two radially internal and external sides (113 and 114) of the latter with respect to the axis of rotation. According to the invention, this device is such that, for at least some of this multitude of cells, these orifices opening into one and the same cell are placed on the same side of a radial line (D) of the ring passing through the axis and through the center of gravity (G) of the cell, seen in radial cross section.

13 Claims, 5 Drawing Sheets

U.S. PATENT DOCUMENTS

| | | | |
|---|---|---|---|
| 4,857,187 A * | 8/1989 | Ito | 210/198.2 |
| 4,877,523 A * | 10/1989 | Nunogaki | 210/198.2 |
| 4,968,428 A * | 11/1990 | Nunogaki | 210/635 |
| 6,537,452 B1 * | 3/2003 | de La Poype et al. | 210/198.2 |
| 7,815,799 B2 * | 10/2010 | Pfeiffer | 210/198.2 |
| 2004/0173534 A1 * | 9/2004 | Margraff et al. | 210/656 |
| 2008/0035546 A1 * | 2/2008 | Foucault et al. | 210/198.2 |
| 2009/0039025 A1 * | 2/2009 | Couillard et al. | 210/657 |
| 2009/0173680 A1 * | 7/2009 | Pfeiffer | 210/198.2 |
| 2010/0200488 A1 * | 8/2010 | Couillard | 210/198.2 |
| 2010/0252503 A1 * | 10/2010 | Foucault et al. | 210/657 |

FOREIGN PATENT DOCUMENTS

| | | |
|---|---|---|
| JP | 56-16868 A | 2/1981 |

* cited by examiner

CENTRIFUGAL PARTITIONING CHROMATOGRAPHY DEVICE AND METHOD IMPLEMENTED BY THIS DEVICE

REFERENCE TO RELATED APPLICATIONS

This application is a 371 of PCT/FR2008/001561 filed Nov. 6, 2008.

FIELD OF THE INVENTION

The present invention relates to a centrifugal partition chromatography device for a liquid having at least two phases, and a centrifugal partition chromatography process used by this device. The invention relates, in particular, to the liquid-liquid separation of two immiscible phases in contact with one another.

BACKGROUND OF THE INVENTION

Centrifugal partition chromatography (CPC) is a method of separating compounds of a mixture between a mobile phase and a stationary phase for each of which the compounds have a different affinity. Known chromatography devices have a stack of flat rings which are rotated about their axis of symmetry and which each have, in a plane perpendicular to this axis, a multitude of cells connected to one another by inlet/outlet ducts or channels for example engraved in these rings. The stationary phase is held immobile inside cells by means of the centrifugal force to which it is subjected due to the rotation of the rings, whilst the mobile phase percolates the stationary phase. Reference may be made, for example, to document FR-A-2 791 578 for the description of such a device.

These devices have a significant gain in productivity, compared to high performance liquid chromatography (HPLC) devices having a packed column, especially due to the following advantages:
- absence of solid stationary phase (relatively expensive), with instead a liquid stationary phase, the regeneration or replacement of which can be carried out in a very short time; and
- significantly higher ratio of stationary phase, which retards the undesirable appearance of nonlinear phenomena and is expressed by a proportional increase of the capacity of the column enabling the elution of compounds at increased concentrations with an inversely proportional mobile phase consumption.

In recent years it has been sought to improve the efficiency of these CPC devices in order to optimize the separations obtained, knowing that this efficiency is essentially based on the flow of the mobile phase through the stationary phase. The effect of the Coriolis acceleration generated by the rotation of the rings on the two-phase flows observed in the cells has thus been demonstrated, as presented, in particular, in the article Mass Transport and Flow Regimes in Centrifugal Partition Chromatography, by L. Marchal, J. Legrand, A. Foucault, AIChE J., 48 (2002) 1692. More specifically, each cell may be divided into three zones comprising an inlet zone where the dispersion of the mobile phase originating from the inlet channel in the form of droplets must be favored, an intermediate zone of curvilinear movement of these droplets and an outlet zone where the coalescence of the droplets before the transfer of the mobile phase into the outlet channel must be favored.

The appended FIGS. 2 and 3, which refer to the aforementioned document FR-A-2 791 578, illustrate the usual arrangement of the two inlet/outlet channels 11 and 12, 11' and 12' of each cell 10, 10' relative to a radial straight line D of the corresponding ring 3, 3' that passes through its axis of rotation X'X and through the barycentre G of the cell 10, 10'. It is seen in FIG. 2 that the two inlet/outlet orifices 11a and 12a via which these channels 11 and 12 open respectively into each cell 10 are both located on this radial straight line D of the ring 3 and, in FIG. 3, that the two inlet/outlet orifices 11a', 12a' of each cell 10' of the ring 3' are located on either side of this straight line D (also visible in FIGS. 2 and 3 are the two inlet and outlet cells 10a and 10b of the ring 3, 3').

In a known manner, a flow of liquid from the radially outer side towards the radially inner side of each cell (i.e. from the periphery toward the center) represents, for the stack of rings, an upflow, whereas conversely a flow toward the radially outer side of each cell (i.e. from the center toward the periphery) represents a downflow, the flow direction being determined by the ratio of the masses of mobile phase and of stationary phase.

SUMMARY OF THE INVENTION

One objective of the present invention is to propose a centrifugal partition chromatography device for a liquid having at least two phases that exhibits an improved chromatographic efficiency compared to that of existing devices, and this objective is achieved in that the applicant has just unexpectedly discovered that if it is chosen to arrange these inlet/outlet orifices of each cell not on the radial straight line, nor on either side of the latter contrary to the prior art, but on one and the same side of this radial straight line, then the coalescence of the droplets is significantly improved in the cell outlet zone at the end of their curvilinear trajectory, due to the deviation that Coriolis acceleration involves as a function of the direction of rotation of the cells, which is expressed by a substantially increased efficiency of the chromatography.

For this purpose, a centrifugal partition chromatography device according to the invention, which comprises at least one flat ring capable of being rotated about its axis of symmetry and comprising a multitude of cells intended to be passed through by the liquid, each cell being provided with two inlet/outlet channels intended to make the liquid flow from one cell to another and opening respectively via two inlet/outlet orifices of the cell on two radially inner and outer sides of the latter relative to said axis, is such that for at least one portion of this multitude of cells, the orifices opening into one and the same cell are arranged on a same lateral side of the radial straight line of the ring that passes through said axis and through the barycentre of this cell, seen in radial cross section.

It will be noted that this radial cross section (i.e. perpendicular to this axis) of each cell in question for the determination of its barycentre, implies that each cell has a constant radial cross section along its direction parallel to the axis of rotation of the or each ring.

It will also be noted that it could be possible to replace this radial straight line with a radial plane containing both this axis of rotation and the center of gravity of each three-dimensional cell in question, taking into account the thickness of this cell in the direction of this axis and therefore without referring to a cell radial cross section.

The expression "lateral side" of this radial straight line is understood in the present description to mean each of the two substantially radial sides of each cell which connect said radially inner and outer sides together.

Advantageously, each of the cells of the or each ring has its two inlet/outlet orifices arranged on one and the same lateral side of said radial straight line.

According to another feature of the invention, for one and the same cell, it is possible to define this arrangement of said orifices strictly on one and the same side of this radial straight line by the fact that the minimum distance between said radial straight line and that of the two orifices which is closest to this straight line is greater than the width of each orifice.

The expression "minimum distance" is understood here to mean the distance measured along a direction perpendicular to this radial straight line (i.e. along a tangential direction for the or each ring), and the term "width of each orifice" is understood to mean the largest transverse dimension of this orifice (e.g. the diameter in the case of a semicylindrical channel that ends with a semicircular orifice).

In other words, it will be noted that this arrangement according to the invention of said inlet/outlet orifices on one and the same side of this radial straight line is thus visible to the naked eye.

Preferably, for a same cell, the ratio of this minimum distance to the length of each of said radially inner and outer cell sides is greater than or equal to 5% and, more preferably still, this ratio is greater than or equal to 30%.

It will be noted that this arrangement according to the invention of the "opening" cross sections or orifices of the inlet ducts or channels in each cell makes it possible to substantially increase the efficiency of the separating operation carried out by means of this device, especially via the optimization of the coalescence at the end of migration of the droplets of mobile phase in each cell.

It will also be noted that this arrangement of the orifices on one and the same side of said radial straight line also contributes to obtaining an improved stability or retention for the stationary phase contained in each cell, in particular on an industrial scale during the injection of large amounts of solutes.

By virtue of this arrangement of the inlet/outlet orifices of cells according to the invention, it is thus advantageously possible to use larger injected amounts of solutes or of solutions and a higher volume flow rate of liquid, which leads to shorter elution times than in the past.

According to a first embodiment of the invention, said sides of each cell provided with corresponding inlet/outlet orifices are symmetrical to one another with respect to an axis of symmetry of this cell, the or each ring then being, for example, intended to be rotated either in the clockwise direction for a flow of liquid through the cell going from the radially outer side toward the radially inner side, or else in the anticlockwise direction for a flow of liquid in the reverse direction.

It will be noted that the direction of rotation to be used for the or each ring according to the invention—which may equally be clockwise or anticlockwise according to this first embodiment—is here determined unequivocally by the reversible flow direction of the liquid, due to the fact that the geometry of each cell is adapted for both flow directions of the liquid.

In accordance with this first embodiment of the invention, each cell may advantageously have a substantially polygonal shape seen in radial cross section, for example substantially rectangular or hexagonal, or else substantially elliptical, in a nonlimiting manner.

According to a second embodiment of the invention, said sides of each cell provided with corresponding inlet/outlet orifices are asymmetrical with respect to one another, the or each ring then being, for example, intended to be rotated:
only in the clockwise direction for a flow of liquid through the cell going from the radially outer side toward the radially inner side, if this inner side has a length greater than that of the outer side, or else
only in the anticlockwise direction for a flow of liquid in the reverse direction if this inner side has a length less than that of the outer side.

In accordance with this second embodiment of the invention, each cell may advantageously have, nonlimitingly, a substantially trapezoidal shape seen in radial cross section, the large and small bases of which are respectively formed by said cell sides provided with said inlet/outlet orifices.

It will be noted that the preferred direction of rotation of the or each ring according to the second embodiment—being only clockwise or only anticlockwise due to the aforementioned asymmetry between the two radially inner and outer sides of each cell—is thus predetermined unequivocally by the geometry of each cell, which is adapted for a single non-reversible flow direction of the liquid.

It will also be noted that this asymmetry of each cell is advantageously designed in order to generate a flow disturbance in the inlet zone of this cell in order to favor the atomization into droplets of the mobile phase, and on the contrary in order to reduce the turbulence of this flow in the outlet zone in order to favor the coalescence of these droplets.

Generally, with reference to these two embodiments of the invention, it will be noted that this direction of rotation is reversed when said inlet/outlet orifices of each cell are both arranged on the other lateral side of said radial straight line.

According to another feature of the invention, the chromatography device may comprise a multitude of said flat rings, with the aforementioned improvement of the chromatographic efficiency.

A centrifugal partition chromatography process for a liquid according to the invention is carried out by a device of the invention as defined above, and this process is such that the direction of rotation of the or each ring about said axis of rotation is chosen as a function of the flow direction of the liquid through each cell so that the or each ring is rotated in the clockwise direction if the liquid flows from the radially outer cell side toward the radially inner cell side or else in the anticlockwise direction if the liquid flows in the reverse direction, or vice versa if said inlet/outlet orifices of each cell are arranged on the other lateral side of said radial straight line.

According to one essential feature of the present invention, it will be noted that the aforementioned arrangement of the inlet/outlet orifices of each cell according to the invention (i.e. on one and the same side of the radial straight line of each ring passing through its axis of rotation and through the barycentre of this cell) implies that the choice of the direction of rotation transmitted to the rings by the rotor of the chromatography device is dictated by the flow direction of the liquid through each cell. In other words, for an arrangement of the inlet/outlet orifices on a predetermined lateral side of this radial straight line of a cell, an upflow direction (i.e. from the periphery toward the center of each cell) imposes a direction of rotation of the rotor only in the clockwise direction, whereas a downflow direction (i.e. from the center toward the periphery of each cell) imposes a direction of rotation of the rotor only in the anticlockwise direction and, for an arrangement of these orifices on the other lateral side of this radial straight line, an upflow direction conversely imposes a direction of rotation of the rotor only in the anticlockwise direction, whereas a downflow direction imposes a direction of rotation of the rotor only in the clockwise direction.

As indicated previously with reference to the first embodiment of the invention, the choice of cells for which the radially outer and inner sides are symmetrical to one another relative to an axis of symmetry of each cell makes it possible to optionally use two flow directions and, consequently, two directions of rotation that they involve.

With reference to the second embodiment of the invention, the or each ring is rotated in a single possible direction of rotation due to the asymmetry between the radially outer and inner sides of each cell, this rotation being carried out:

- in the clockwise direction, if the liquid flows from the radially outer side toward the radially inner side of each cell, due to the fact that this inner side has a length greater than that of the outer side, or conversely (i.e. in the anticlockwise direction) if said inlet/outlet orifices are arranged on the other lateral side of said radial straight line; and
- in the anticlockwise direction if the liquid flows from the radially inner side toward the radially outer side of each cell, due to the fact that this inner side has a length of less than that of the radially outer side, or conversely (i.e. in the clockwise direction) if said orifices are arranged on the other lateral side of said radial straight line.

BRIEF DESCRIPTION OF THE DRAWINGS

The aforementioned features of the present invention, and also other features, will be better understood on reading the following description of several exemplary embodiments of the invention, given by way of illustration and nonlimitingly, said description being made in relation to the appended drawings, among which.

DETAILED DESCRIPTION

Figure 1:
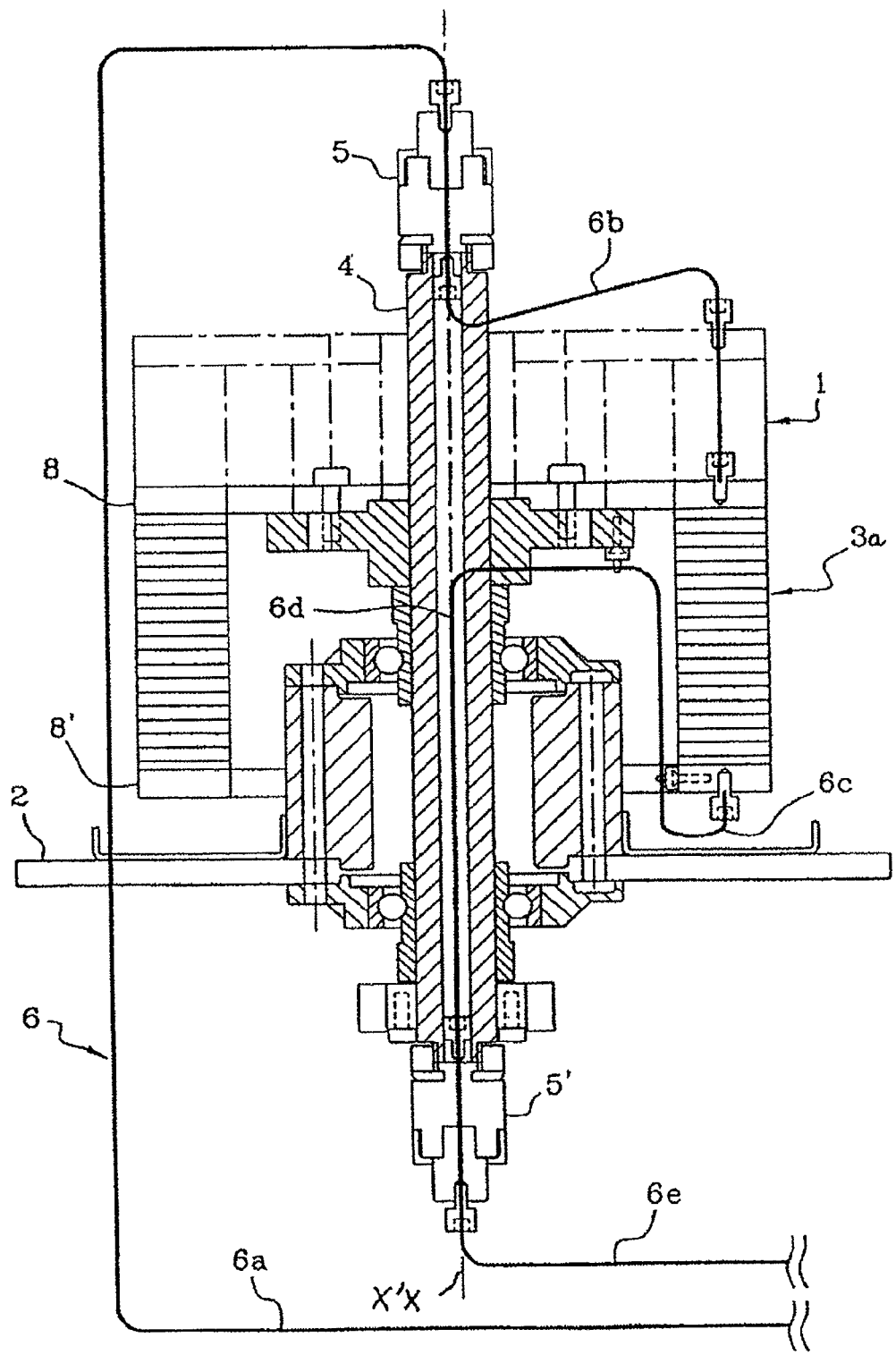
FIG. 1 is an axial cross-sectional view in a vertical plane of a centrifugal partition chromatography device according to one exemplary embodiment of the invention.
Figure 2:
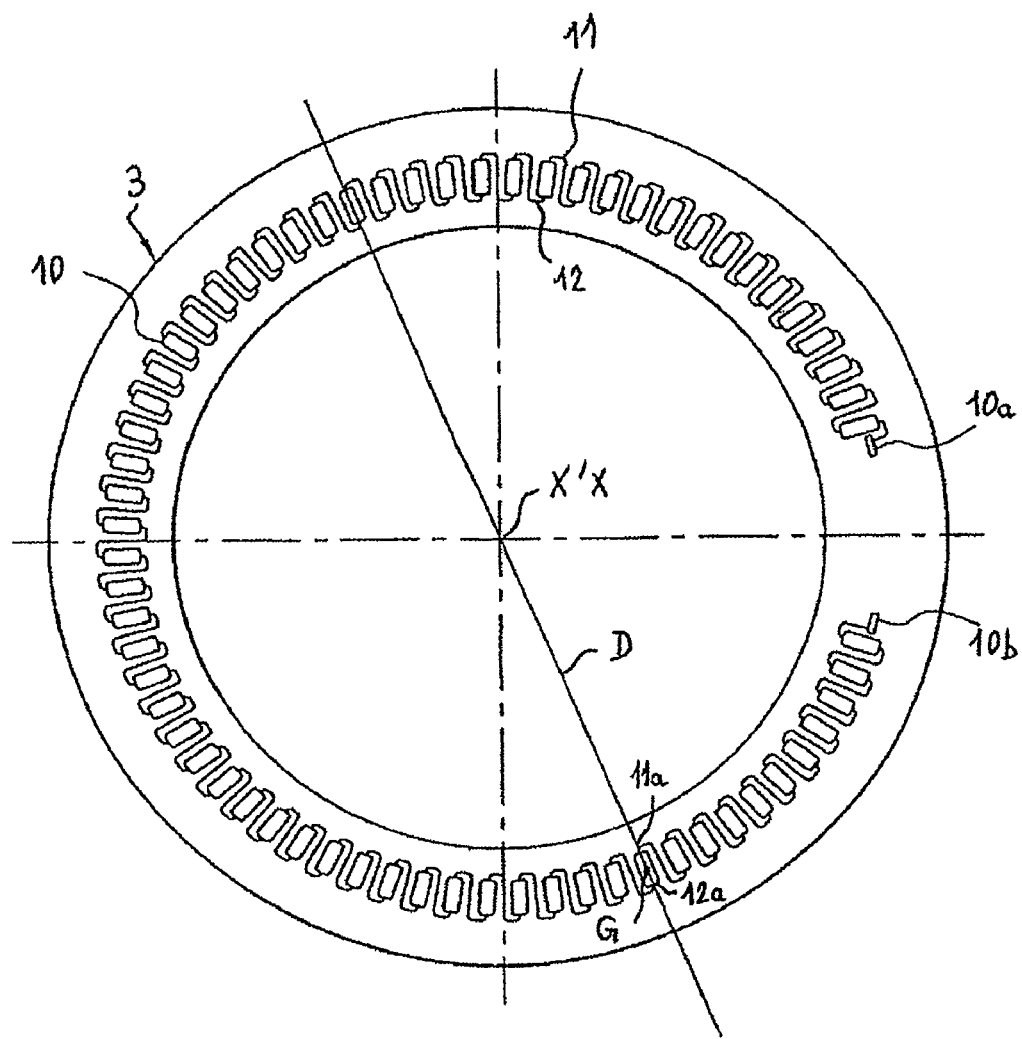
FIG. 2 is a schematic top view of a known ring that can be used in the device of FIG. 1, where the cells are arranged according to the prior art.
Figure 3:
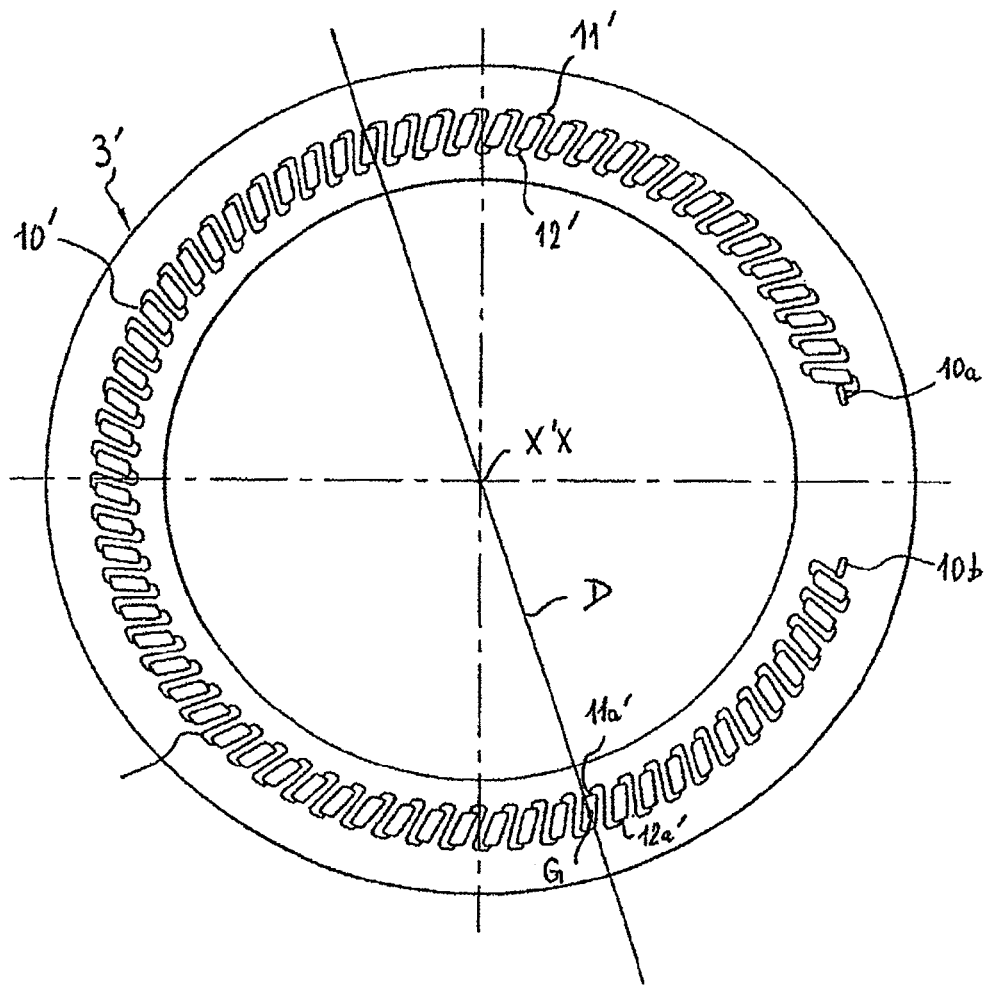
FIG. 3 is a schematic top view of a known ring variant that can be used in the device of FIG. 1, where the cells are also arranged according to the prior art.

As illustrated in FIG. 1, a centrifugal partition chromatography device according to the invention comprises a rotor 1 mounted on a table 2 and able to be rotated about an axis X'X positioned vertically in the example of FIG. 1, by means of known drive means that are not represented. The rotor 1 is constituted of several stacked flat rings 3a, of the same diameter and that are fastened to a column 4 of known structure formed from a hollow tube positioned between two top 5 and bottom 5' rotating joints. The axis of rotation X'X corresponds to the axis of the stacked rings 3a. The column 4 is supplied with liquid through the joints 5 and 5' via a piping system 6 connected to known feed and recovery means that are not illustrated.

Since the device is capable of operating in two respectively upflow and downflow directions, each of the two rotating joints 5 and 5' may constitute either the inlet or the outlet of the system, the path of the liquid in the circuit 6 being marked by a bold line in FIG. 1.

In the case of a downflow operation for example, a first branch 6a of the circuit 6 connects the feed means (such as a pump) to the upper rotating joint 5. After having passed through this joint 5, a second branch 6b conveys the liquid to the inlet of the rotor 1 and, after having passed through it, emerges at the bottom part at the branch 6c. The branch 6d, located inside the column 4, conveys the liquid to the lower rotating joint 5' which, after having passed through it, is recovered at the branch 6e, and transported toward the recovery means.

Thus, the pressurized liquid enters at the upper joint 5 in order to reach, via the top, the stack of rings 3a by passing through the column 4, then flows inside the cells of the first ring 3a, then those of the second and so on, in order to emerge at the lower level of the stack of rings 3a and pass through the column 4 down to the lower rotating joint 5'. If the device operates in upflow mode, the course of the liquid is reversed.

Figure 4:
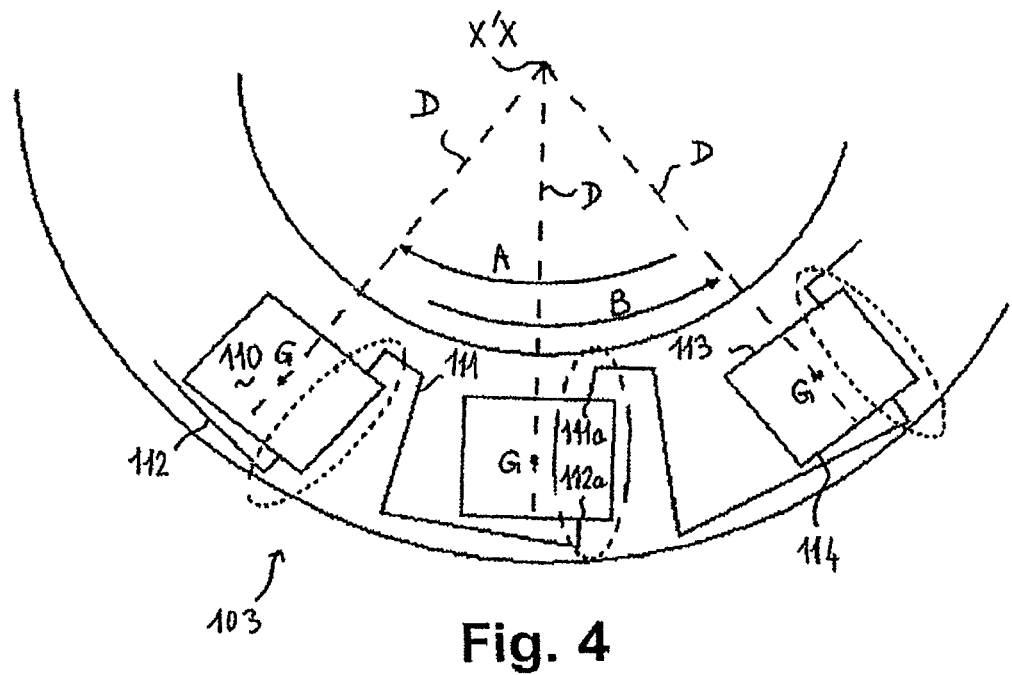
FIG. 4 is a partial and top schematic view of a ring according to the invention that can be used in the device of FIG. 1 and is designed in order to be rotated in both directions of rotation, where the cells are arranged in accordance with the first embodiment of the invention.
Figure 5:
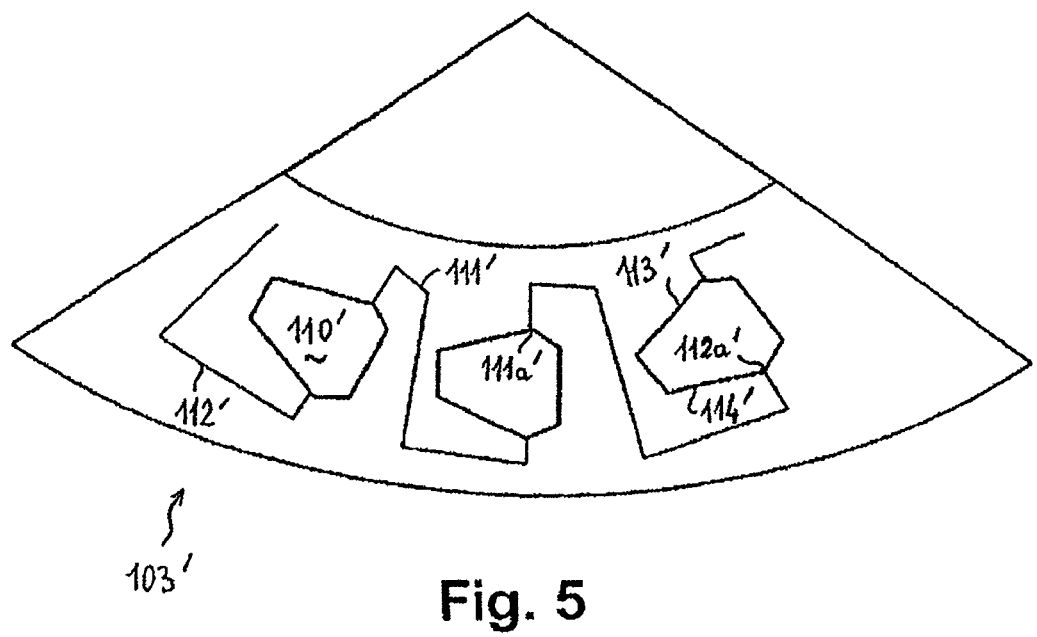
FIG. 5 is a partial and top schematic view of another ring according to this first embodiment of the invention that can be used in the device of FIG. 1 and is designed in order to be rotated in both directions of rotation, where the cells are arranged according to a variant of FIG. 4.

FIGS. 4 and 5 partially illustrate two examples of rings 103, 103' for which the cells 110, 110' are connected together by inlet/outlet channels 111 and 112, 111' and 112' arranged according to the first embodiment of the invention. As is shown by the dotted line insets surrounding the respective inlet/outlet orifices 111a and 112a, 111a' and 112a' of the channels 111 and 112, 111' and 112' in each of the three cells 110, 110' represented, these orifices are located on one and the same lateral side of the radial straight line D (represented by dashes) of the ring 103, 103' passing through its axis of rotation X'X and through the barycentre G of each cell 110, 110', in a radial cross section of the latter (i.e. a horizontal cross section in the example of these FIGS. 4 and 5).

According to one important feature of the invention which is linked to this arrangement of the orifices 111a and 112a, 111a' and 112a' on one and the same side of the straight line D, which in the example of FIGS. 4 and 5 is the right-hand side for an observer positioned above the device, the upflow or downflow direction of the liquid in the device (i.e. radially toward the inside or radially toward the outside of each cell 110, 110' respectively) dictates the choice of the direction of rotation of the rings 103, 103' via the movement of the rotor 1.

In the first example of rings 103 according to FIG. 4, each cell 110 has, in radial cross section, a rectangular shape delimited radially by two large radially inner 113 and outer 114 sides which are perpendicular to the radial direction of the straight line D, and the inlet/outlet orifices 111a and 112a are each separated from this straight line D by a distance which, measured along these large sides 113 and 114, is greater than 30% of the length of these sides 113 and 114.

Due to the symmetry of each cell 110 relative to its longitudinal axis of symmetry parallel to the large sides 113 and 114, which means that the latter and the orifices 111a and 112a with which they are provided are of the same length and are arranged identically, it is possible to optionally use the device incorporating the rings 103 of FIG. 4 in one or other of the two upflow and downflow directions, it being specified that:

if the liquid is made to flow in the upflow direction (i.e. from the outer side 114 toward the inner side 113 of each cell 110) then it is chosen to rotate the rings 103 in the clockwise direction (arrow A) in the example of FIG. 4; and that if the liquid is made to flow in the downflow direction (i.e. from the inner side 113 toward the outer side 114 of each cell 110) then it is chosen to rotate the rings 103 in the anticlockwise direction (arrow B) still in the example of FIG. 4.

This free choice of the flow direction and therefore of the direction of rotation which results therefrom for the rings 103 is due to the fact that the inlet and outlet zones of each cell 110, where the dispersion of the droplets of mobile phase penetrating into the cell 110 and their coalescence before exiting therefrom are respectively carried out, are interchangeable (i.e. reversible for the flow direction of the liquid), due to the aforementioned symmetry.

In the second example of FIG. 5, each cell 110' has, in radial cross section, a hexagonal shape delimited radially by two pairs of large sides which are respectively radially inner 113' and outer 114' for the cell 110' and which are symmetrical to one another relative to the longitudinal axis of symmetry of the cell 110'.

Following the example of FIG. 4, it results from this symmetry that it is possible to optionally use the device incorporating the rings 103' of FIG. 5 in one or the other of the two flow directions, it being specified that in the upflow direction (i.e. from the outer side 114' toward the inner side 113' of each cell 110), it is chosen to rotate the rings 103' in the clockwise direction in the example of FIG. 5, whereas in the downflow direction (i.e. from the inner side 113' toward the outer side 114') it is chosen to rotate the rings 103' in the anticlockwise direction according to the same example.

Figure 6:
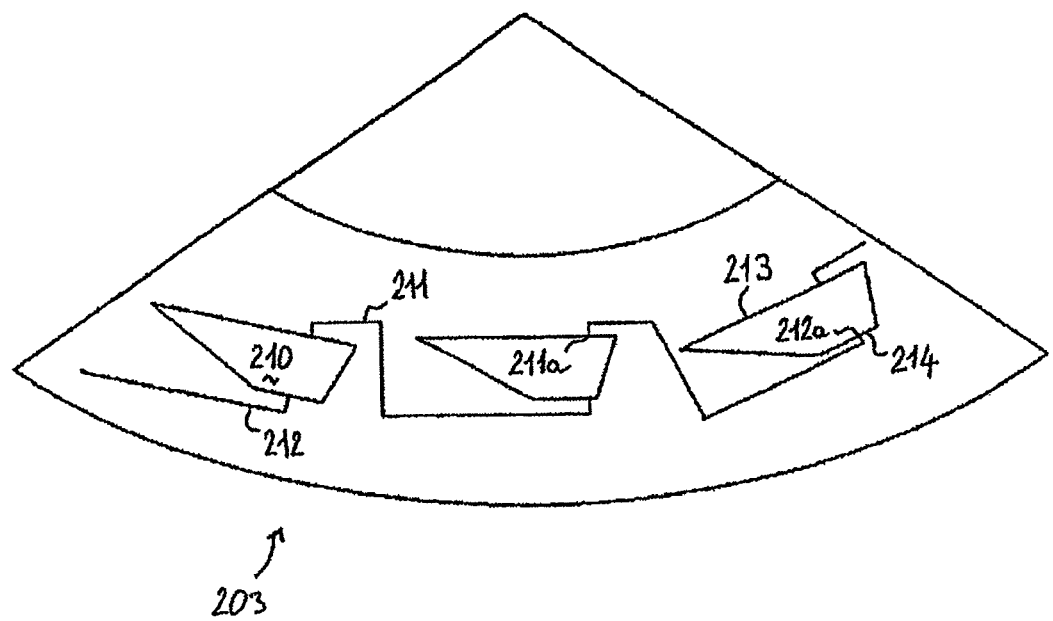
FIG. 6 is a partial and top schematic view of another ring according to the invention that can be used in the device of FIG. 1 and is designed in order to be rotated in the clockwise direction only, where the cells are arranged according to the second embodiment of the invention.
Figure 7:
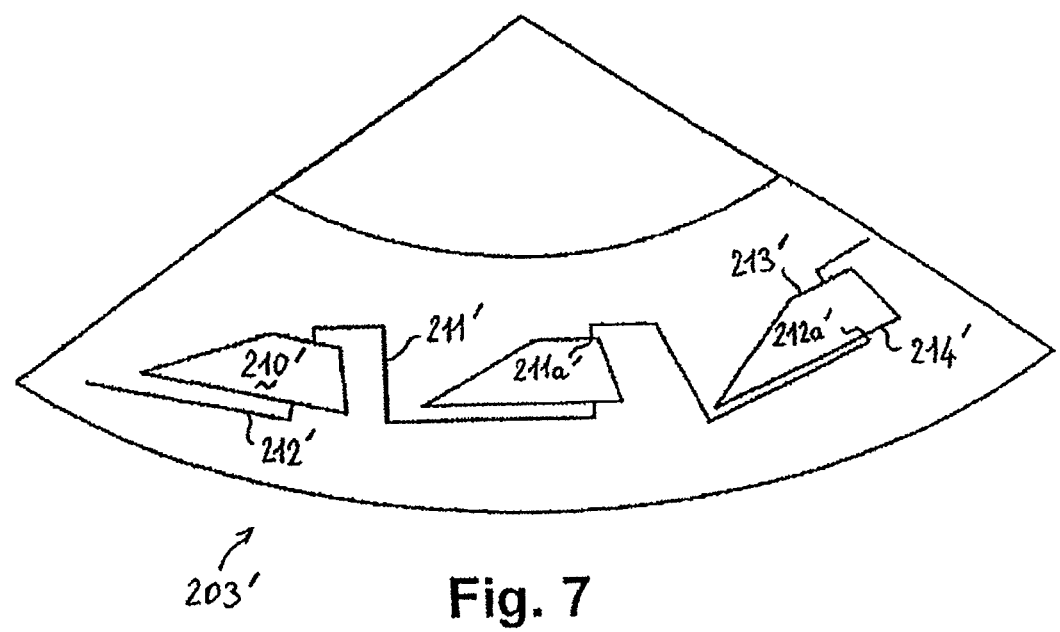
FIG. 7 is a partial and top schematic view of another ring according to the invention that can be used in the device of FIG. 1 and is designed in order to be rotated in the anticlockwise direction only, where the cells are also arranged according to the second embodiment of the invention.

In the second embodiment of the invention illustrated in FIGS. 6 and 7, each cell 210, 210' of the ring 203, 203' has an asymmetrical shape which is, for example, trapezoidal seen in radial cross section, and of which:

in FIG. 6, the large base 213 and the small base 214 respectively form the radially inner and outer sides of each cell 210 provided with inlet/outlet orifices 211a and 212a, these cells 210 being specifically designed for a solely upflow liquid flow (i.e. from the small base 214 to the large base 213, in order to favor the atomization and the coalescence of the droplets of mobile phase at the inlet and at the outlet of the cell) and, consequently, for a rotation specifically implemented via the rotor 1 in the clockwise direction in the example of FIG. 6 where the orifices 211a and 212a are arranged on the right-hand side of the radial straight line of each cell 210 for an observer positioned above the device; and in FIG. 7, the small base 213' and the large base 214' respectively form the radially inner and outer sides of each cell 210' provided with inlet/outlet orifices 211a' and 212a', these cells 210' being specifically designed for a solely downflow liquid flow (i.e. from the small base 213' to the large base 214', in order to favor the atomization and the coalescence of the droplets in the inlet and outlet zones) and, consequently, for a rotation specifically implemented via the rotor 1 in the anticlockwise direction in the example of FIG. 7 where the orifices 211a' and 212a' are also arranged on the right-hand side of the radial straight line of each cell 210' for an observer positioned above the device.

It will be noted that the direction of rotation of the rings 203, 203' according to the second embodiment is thus predetermined unequivocally by the asymmetric geometry of each cell 210, 210', which is adapted for a single flow direction of the liquid, while observing that the clockwise or anticlockwise directions of rotation respectively dictated by these upflows or downflows would be reversed in the case of inlet/outlet orifices of cells arranged not to the right but to the left of said radial straight line, as variants of FIGS. 6 and 7.

Generally, it will be noted that the geometry of the cells 110, 110' and 210, 210' and of the channels 111, 112, 111', 112', 211, 212, 211', 212' illustrated in FIGS. 4 to 7 according to the invention is in no way limiting, and that the substantially radial connecting portions of these channels to the corresponding cells could have different orientations and/or lengths. In particular, the intermediate sections of these channels 111, 112, 111', 112', 211, 212, 211', 212' which are, in these figures, perpendicular in pairs and three in number, could have relative lengths and/or orientations that are also different from those illustrated.

The invention claimed is:

1. A centrifugal partition chromatography device for a liquid having at least two phases, the device comprising at least one flat ring which is capable of being rotated about its axis of symmetry and which comprises a multitude of cells intended to be passed through by the liquid, each cell being provided with two inlet/outlet channels which are intended to make the liquid flow from one cell to another and which open respectively via two inlet/outlet orifices of the cell on two radially inner and outer sides of the latter relative to said axis of rotation, characterized in that for at least one portion of this multitude of cells, said orifices opening into one and the same cell are arranged on a same lateral side of a radial straight line of the ring that passes through said axis and through the barycentre of this cell, seen in radial cross section.

2. The device as claimed in claim 1, characterized in that each cell of the or each ring has its two inlet/outlet orifices arranged on a same lateral side of said radial straight line.

3. The device as claimed in claim 1, characterized in that, for a same cell, the minimum distance between said radial straight line and that of the two orifices which is closest to this straight line is greater than the width of each orifice.

4. The device as claimed in claim 3, characterized in that, for a same cell, the ratio of this minimum distance to the length of each of said radially inner and outer cell sides is greater than or equal to 5%.

5. The device as claimed in claim 4, characterized in that, for a same cell, this ratio is greater than or equal to 30%.

6. The device as claimed in claim 1, characterized in that said sides of each cell provided with corresponding inlet/outlet orifices are symmetrical to one another with respect to an axis of symmetry of this cell, the or each ring being, for example, intended to be rotated either in the clockwise direction for a flow of liquid through the cell going from the radially outer side toward the radially inner side, or else in the anticlockwise direction for a flow of liquid in the reverse direction.

7. The device as claimed in claim 6, characterized in that each cell has a substantially polygonal shape seen in radial cross section, for example substantially rectangular or hexagonal, or else substantially elliptical.

8. The device as claimed in claim 1, characterized in that said sides of each cell provided with corresponding inlet/outlet orifices are asymmetrical with respect to one another, the or each ring being, for example, intended to be rotated:

only in the clockwise direction for a flow of liquid through the cell going from the radially outer side toward the radially inner side, if this inner side has a length greater than that of the outer side, or else only in the anticlockwise direction for a flow of liquid in the reverse direction if this inner side has a length less than that of the outer side.

9. The device as claimed in claim 8, characterized in that each cell has a substantially trapezoidal shape seen in radial cross section, the large and small bases of which are respectively formed by said cell sides provided with said inlet/outlet orifices.

10. The device as claimed in claim 1, characterized in that it comprises a multitude of said flat rings.

11. A centrifugal partition chromatography process for a liquid having at least two phases used by a device as claimed in claim 1, comprising the step of selecting a direction of rotation of each ring about said axis of rotation is chosen as a function of the flow direction of the liquid through each cell so that the or each ring is rotated in the clockwise direction if the liquid flows from said radially outer cell side toward said radially inner cell side or else in the anticlockwise direction if the liquid flows in the reverse direction, or vice versa if said inlet/outlet orifices of each cell are arranged on the other lateral side of said radial straight line.

12. The process as claimed in claim 11, characterized in that the or each ring is rotated in the clockwise direction if the liquid flows from the radially outer side toward the radially inner side of each cell and if this radially inner side has a length greater than that of the radially outer side, or conversely if said inlet/outlet orifices of each cell are arranged on the other lateral side of said radial straight line.

13. The process as claimed in claim 11, characterized in that the or each ring is rotated in the anticlockwise direction if the liquid flows from the radially inner side toward the radially outer side of each cell and if this radially inner side has a length less than that of the radially outer side, or conversely if said inlet/outlet orifices of each cell are arranged on the other lateral side of said radial straight line.

* * * * *

UNITED STATES PATENT AND TRADEMARK OFFICE
CERTIFICATE OF CORRECTION

PATENT NO.       : 8,182,690 B2                             Page 1 of 1
APPLICATION NO.  : 12/742509
DATED            : May 22, 2012
INVENTOR(S)      : Foucault et al.

It is certified that error appears in the above-identified patent and that said Letters Patent is hereby corrected as shown below:

Column 9,
Line 14, "said axis of rotation is chosen" should read --said axis of rotation--.

Signed and Sealed this
Seventh Day of August, 2012

David J. Kappos
*Director of the United States Patent and Trademark Office*